US006541275B1

(12) United States Patent
Ruiz et al.

(10) Patent No.: US 6,541,275 B1
(45) Date of Patent: Apr. 1, 2003

(54) IMMUNOASSAY FOR F1.2 PROTHROMBIN FRAGMENT

(75) Inventors: Juan A. Ruiz, Miami, FL (US); James R. Maynard, Miami, FL (US); Frederick Dombrose, Ventura, CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 07/151,735

(22) Filed: Feb. 3, 1988

(51) Int. Cl.$^7$ ..................... G01N 33/543; G01N 33/573
(52) U.S. Cl. ................... 436/518; 435/7.4; 435/7.94; 436/547; 436/548; 530/387.9
(58) Field of Search ................. 435/7, 13, 7.1, 435/7.4, 7.9, 7.94, 172.2, 240.27; 436/548, 531, 821, 518, 524, 520, 528, 547; 530/387, 387.9

(56) References Cited

U.S. PATENT DOCUMENTS

| | | |
|---|---|---|
| 4,287,180 A | 9/1981 | Thomas et al. ............. 424/101 |
| 4,289,498 A | 9/1981 | Baughman et al. |
| 4,334,018 A | 6/1982 | Kirchhof ..................... 435/13 |
| 4,357,321 A | 11/1982 | Thomas et al. ............. 424/101 |
| 4,459,288 A | 7/1984 | Thomas et al. ............. 424/101 |
| 4,465,623 A | 8/1984 | Chanas et al. |
| 4,663,164 A | 5/1987 | Thomas et al. ............. 424/101 |
| 4,668,621 A | 5/1987 | Doellgast ..................... 435/13 |

FOREIGN PATENT DOCUMENTS

| | | | |
|---|---|---|---|
| EP | 0151239 | | 8/1985 |
| EP | 88113124.7 | | 8/1988 |
| EP | 0303983 | * | 2/1989 |

OTHER PUBLICATIONS

Bidart et al. "Identification of Epitopes Associated With HCG and the B HCG Carboxyl Terminus by Monoclonal Antibodies Produced Against a Synthetic Peptide" J. Immunology vol. 134 No. 1, Jan. 1985 pp. 457–464.*
H. Lau et al., The Isolation and Characterization of a Specific Antibody Population Directed Against the Prothrombin Activation Fragments F2 and F1&2, 234 J. Biological Chemistry 8751 (1979).
G. Walter, "Antibodies Specific for the Carboxy–and amino–terminal Regions of Simian Virus 40 Large Tumor Antigen," 77 Proc. Nat'l Acad. Sci. 5197 (1980).
J. Teitel et al., "Studies of Prothrombin Activation Pathway Utilizing Radioimmunoassays for F2/F1&2 Fragment and Thrombin–Antithrombin Complex," 59 Blood 1086 (1982).
G. Walter et al., "Cross–Reactivity of Antibodies Against Synthetic Peptides," 19 J. Cellular Biochem. 119 (1982).
K. Hui et al., "Monoclonal Antibodies to a Synthetic Fibrin––Like Peptide Bind to Human Fibrin but not Fibrinogen, " Dec. 9, 1983.
Niman et al., "Generation of protein–reactive antibodies by short peptides is an event of high frequency: Implications for the structural basis of immune rejection," 80 Proc. Nat'l Acad. Sci. 4949 (1983).
Pacella et al., "Induction of Fibrin–Specific Antibodies by Immunization with Synthetic Peptides that Correspond to Amino Termini of Thrombin Cleavage Sites, " Cellular Immuno 521 (1983).
A. Bezeaud, "Quantitation of Prothrombin Activation Products in Human Urine" 58 British J. Haematology 597 (1984).
Lerner, "Antibodies of Predetermined Specificity in Biology and Medicine," Advance in Immunology v. 36 (1984).
Friquet et al., "Measurements of True Affinity Constant in Solution of Antigen–Antibody Complexes by Enzyme–Linked Immunosorbent Assay," J. Immuno Methods 305 (1985).
A. Moriarty et al., "Antibodies to Peptides Detect New Hepatitis B Antigen: Serological Correlation with Hepatocellular Carcinoma,"227 Science 429 (1985).
Muller–Berghaus et al., "Detection of Fibrin in Plasma by a Monoclonal Antibody Against the Amino–terminus of the Alpha–chain of Fibrin," 45 Scand. J. Clin. Inves. 145 (1985).
Scheefers–Borchet et al., "Discrimination between Fibrin and Fibrinogen by a Monoclonal Antibody Against a Synthetic Peptide," 82 Proc. Natl. Acad. Sci. 7091 (1985).
Abstract, "Detection of Prothrombin Activation Fragments F2/F1&2 by an Antibody Against a Synthetic Peptide," German Congress for Thrombosis, Frankfort, Feb. 24–27, 1988.

* cited by examiner

*Primary Examiner*—Patricia A. Duffy
(74) *Attorney, Agent, or Firm*—Edwards & Angell, LLP

(57) ABSTRACT

According to the present invention highly specific-low affinity antibodies are generated which allow for the assay of F1.2 in bodily fluids that also contain prothrombin or other plasma proteins. Antibodies having the necessary properties for this assay are made using synthetic polypeptides which mimic the carboxy terminus of F1.2.

4 Claims, 2 Drawing Sheets

IMMUNOASSAY FOR F1.2 PROTHROMBIN FRAGMENT

BACKGROUND OF THE INVENTION

This invention relates to chemically synthesized immunogens which generate antibodies specific for the activation peptide from prothrombin, F1.2. In another aspect, it relates to methods for detecting the presence and/or concentration of F1.2 in plasma.

Many proteins are synthesized in vivo as inactive precursors, or zymogens, which are subsequently converted to their active forms by limited proteolysis. This process of zymogen activation is a rate-limiting step in a variety of physiological processes which include blood coagulation. Blood coagulation proteins are "activated" by highly specific, limited peptide bond cleavage, which generate new carboxy and amino termini. The amino acid sequence within these termini is highly specific for a particular coagulation protein. These termini which are often located at the surface of the protein, show a relatively high conformational flexibility and are frequently good antigenic determinants.

Prothrombin is one of a series of proteins that participate in the blood clotting mechanism. Thrombin has many functions including catalyzing the conversion of fibrinogen to fibrin, and thus preventing the loss of blood from the vascular system of vertebrates. Prothrombin is proteolytically cleaved to form its active state thrombin; in this conversion the polypeptide fragment F1.2 is formed.

The detection of prothrombin activation products within whole blood or plasma has been attempted using immunological methods, but has been impaired because of the cross-reactions between the activation products and the parent molecule. Studies on radioimmunologic techniques for F1.2 in human plasma, have shown that there is significant cross-reactivity between F1.2 and related proteins such as F1, prothrombin and prethrombin-2. Cross-reactivities between the activation product and prothrombin, thus preclude the quantitation of this fragment in whole blood. In addition, the concentration of prothrombin is exceedingly high compared with the minute quantities of activation fragment that is expected to be formed in vivo.

The isolation of specific antibody population directed against cleavage fragments has allowed for the demonstration of small amounts of F1.2 in normal human plasma, even in the presence of normal prothrombin levels. Lau et al., *The Isolation and Characterization of Specific Antibody Population Directed Against the Prothrombin Activation Fragments F2 and F1+2*, 254 J. Bio. Chem. 8751 (1979). Additionally, Prothrombin catabolism has also been studied by screening urine for prothrombin derivatives. Bezeaud et al., *Identification of Prothrombin Derivatives in Human Urine,* 13 Thrombin Res. 551 (1978). Further studies by this group showed that in urine, where prothrombin is absent, it was possible to accurately quantitate F1 and F2 fragments. Bezeaud et al, *Quantitation of Prothrombin Activiation Products in Human Urine,* 58 Brit. J. Haemat. 597 (1984).

SUMMARY OF THE PRESENT INVENTION

According to the present invention, highly specific—low affinity antibodies are generated which allow for the assay of F1.2 in bodily fluids that also contain prothrombin, or other plasma proteins. The antibodies are made using synthetic polypeptides which mimic the carboxy terminus of F1.2. The synthetic polypeptide of this invention elicited antibodies specific for F1.2, but which do not bind to intact prothrombin or other plasma proteins. This specificity is of particular importance in measuring F1.2 in plasma since prothrombin is normally present in a 1000-fold molar excess over F1.2.

Many different peptides were synthesized. The specific synthetic polypeptide used to raise antibodies with the highest specificity for F1.2 was found to have the following amino acid sequence: [CYS-GLY]-ASP-ARG-ALA-ILE-GLU-GLY-ARG-OH. Glycine and cysteine residues were added to permit convenient attachment of the synthetic polypeptide to a carrier protein. These additional amino acids (CYS-GLY), however, are not critical to this invention. This polypeptide-protein conjugate was used to elicit an immune response in laboratory animals.

STATEMENT OF THE INVENTION

Figure 1:
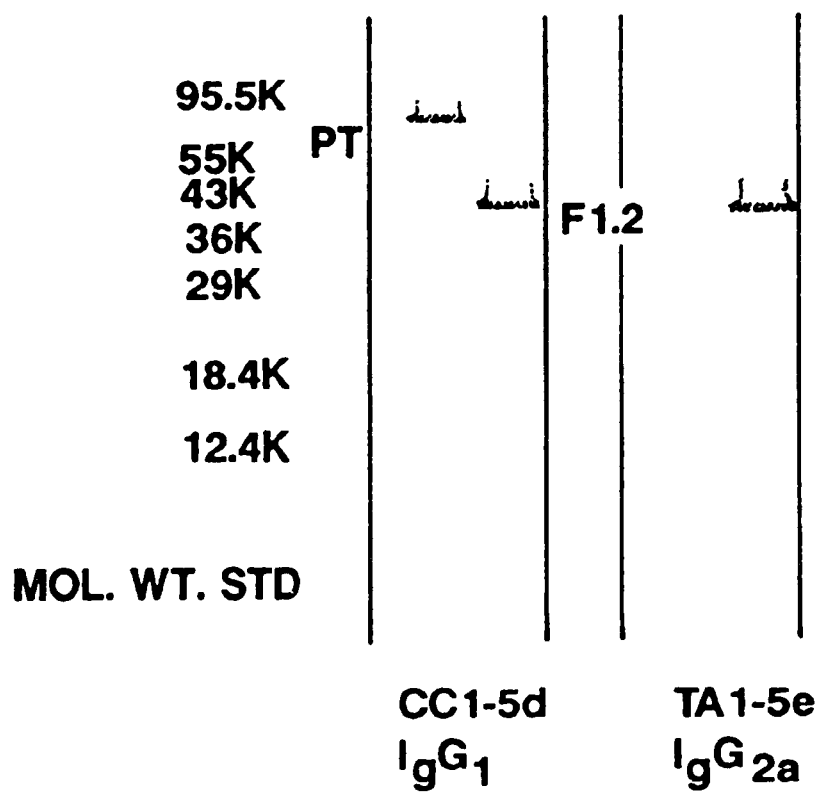
FIG. 1 illustrates the Western Blot of prothrombin and F1.2 developed with monoclonal antibodies TA1-5e and CC1-5d.
Figure 2:
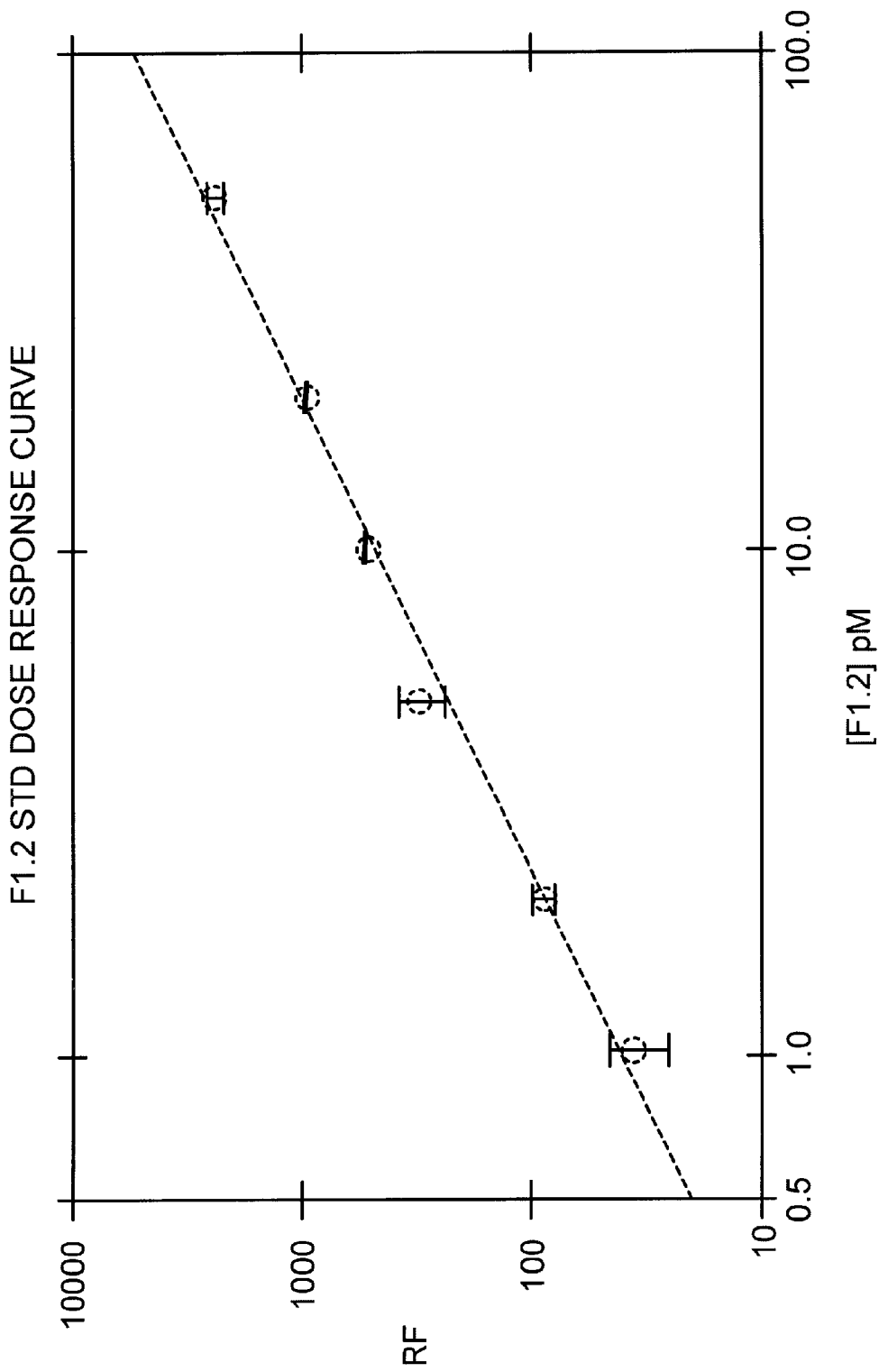
FIG. 2 illustrates the F1.2 standard dose response curve.

Tests have been devised to determine the presence or amount of the F1.2 in body fluids. Current radioimmunoassays of prothrombin activation fragments in human plasma have shown that related proteins such as F1, prothrombin and prothrombin-1 and prethrombin-2 have significant cross-reactivity with F1.2. This cross-reactivity and the low concentration of F1.2 have made the quantitation of F1.2 in plasma difficult. Teitel et al., *Studies of the Prothrombin Activation Pathway Utilizing Radioimmunoassay for the F2/F1+2 Fragment and Thrombin-Antithrombin Complex* 59 Blood 1086, (1982). In the late 1970's, a radioimmunoassay was developed which attempted to minimize cross-reactivities by using a selected population of polyclonal antibodies to F1.2 See Lau et al, *The Isolation and Characterization of a Specific Antibody Population Directed Against the Prothrombin Activation Fragments F2 and F1+2* 234 J. Bio. Chem. 8751 (1979).

In the present invention, specific synthetic peptides are used as immunogens to elicit highly specific-low affinity antibodies for F1.2. The synthetic polypeptides are formed using solid-phase peptide synthesis according to the procedures stated in Hudson et al., *High Yielding Fully Automatic Synthesis of Cecropin A Amide and Analogues* Peptide Chemistry p. 413 (1985). The synthetic peptides mimic the carboxy terminus of the F1.2 polypeptide fragment.

Immunization with these peptides results in highly specific antibodies for F1.2. These antibodies do not bind intact prothrombin or other plasma proteins. The amino acid length of the preferred synthetic peptide is seven amino acids residues. We have observed that shorter synthetic peptides have significant sequence homology to other coagulation proteins and larger synthetic peptides may contain multiple antigenic determinants; these properties could result in antibodies with cross-reactivities to other plasma proteins.

In addition, the peptides can be synthesized with additional glycine and cysteine residues at the amino terminus; these residues are not found in the natural sequence. Glycine serves as a spacer between the synthetic peptide and the carrier protein; cysteine provides a convenient attachment point of the synthetic peptide to a carrier protein. This method of attachment controls how the antigenic determinant is presented to the immune system. The critical antigenic region is positioned away from the bulk of the carrier protein, thus providing easy access for immune response and a better mimic of the native conformation of the F1.2 polypeptide.

The following is a summary of the peptides which were prepared to mimic F1.2 and prothrombin- polypeptide fragments (Table I).

shown in example III, it is the capture antibody in this assay that permits the quantitation of F1.2 in the presence of excess circulating prothrombin.

Direct quantitative comparison by ELISA of monoclonal antibodies TA1-5e, CC1-5d (a monoclonal antibody made by immunizing animals with the polypeptide F1.2) and a

TABLE I

DETAILED DIAGRAM OF SYNTHETIC PEPTIDES

| 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | | 1 | 2 | 3 | 4 | 5 | 6 | 7 | 8 | 9 | 10 | 11 | 12 | 13 |
|---|---|---|---|---|---|---|---|---|---|---|---|---|---|---|---|---|---|---|---|---|---|---|---|---|---|---|---|---|---|---|---|---|---|---|---|---|
| -E | -E | -A | -V | -E | -E | -E | -T | -G | -D | -G | -L | -D | -E | -D | -S | -D | -R | -A | -I | -E | -G | -R | | A | -T | -A | -T | -S | -E | -Y | -Q | -T | -F | -F | -N | -P | -R |
| ---------------------------------- F1.2 ---------------------------------------- ] | | | | | | | | | | | | | | | | | | | | | | | | [ ----------- PRETHROMBIN 2 --------- |

Peptide C7COOH comprises residues 1 to 7 to the left of the Xa cleavage site (free carboxyl group)
Peptide C12OH comprises residues 1 to 12 to the left of the Xa cleavage site (free carboxyl group)
Peptide C12NH2 comprises residues 1 to 13 to the left of the Xa cleavage site (blocked carboxyl group)
Peptide C23NH2 comprises residues 1 to 23 to the left of the Xa cleavage site (blocked carboxyl group)
Peptide C23—10NH2 comprises residues 10 to 23 to the left of the Xa cleavage site (blocked carboxyl group)
Peptide C12N13 comprises residues 1 to 12 to the left of the Xa cleavage site and residues 1 to 13 to the right of the Xa cleavage site The specificity of antibodies to F1.2 elicited using synthetic immunogens is high as shown by ELISA using various antigens and synthetic peptides. The affinities of these antibodies for F1.2, however, is surprisingly low. Low-affinity to a particular antigen may be a general characteristic of antibodies elicited via synthetic peptide which mimic an antigen. Preferably the antibodies have affinity constants of less than about $1 \times 10^8$ L/M. Affinity constants were determined by the method of Friguet et al., *Measurements of the True Affinity Constant in Solution of Antigen-Antibody Complexes by Enzyme-Linked Immunoabsorbent Assay*, 77 Immuno. Methods, 305 (1985).

One monoclonal antibody, made by the presently described process, discussed in example 1A, has an affinity constant for F1.2 of $5.37 \times 10^5$ L/M (TA1-5e). TA1-5e (IgG2a kappa subclass) has been used in a "sandwich" assay for F1.2 as the "capture" antibody. In the present invention, as polyclonal antibody identical to the one described by Teitel et al., *Studies of the Prothrombin Activation Pathway Utilizing Radioimmunoassay for the F2/F1+2 Fragment and Thrombin-Antithrombin Complex*, 59 Blood 1086 (1982), for specificity to a series of synthetic peptides, F1.2 and prothrombin (PT), show the differential sensitivity of the antibodies. Monoclonal antibody TA1-5e only binds to F1.2 and the seven amino acid peptide (AP2/C7OH). TA1-5e does not bind to prothrombin or peptides which contain amide blocked c-terminus. Monoclonal antibody CC1-5d binds F1.2 and prothrombin, but none of the synthetic peptides. The polyclonal antibody binds to F1.2, prothrombin and the seven amino acid peptide (AP2/C7OH) (See Table II).

TABLE II

F1°2, PT, and Peptide Incubation with CCl-5d Ascites

| DILUTION X1000 | F1°2 | PT | AP2/C7OH | AP2/C12OH | AP2/C12NH2 | AP2/C23NH2 | AP2/C23-10 | AP2/C12N13 |
|---|---|---|---|---|---|---|---|---|
| 10 | 1.68 | 1.75 | 0.01 | 0.01 | 0.01 | 0.01 | 0 | 0 |
| 20 | 1.62 | 1.74 | 0.01 | 0.00 | 0.00 | 0.00 | 0 | 0 |
| 40 | 1.47 | 1.69 | 0.01 | 0.01 | 0.01 | 0.02 | 0 | 0 |
| 80 | 1.15 | 1.57 | 0.00 | 0.00 | 0.00 | 0.00 | 0 | 0 |
| 160 | 0.80 | 1.35 | 0.01 | 0.00 | 0.00 | 0.01 | 0 | 0 |
| 320 | 0.42 | 0.88 | 0.00 | 0.00 | 0.00 | 0.00 | 0 | 0 |
| 640 | 0.25 | 0.52 | 0.00 | 0.00 | 0.00 | 0.01 | 0 | 0 |
| BLANK | 0.00 | 0.00 | 0.00 | 0.00 | 0.00 | 0.00 | 0 | 0 |

F1°2, PT, and Peptide Incubation with Rabbit Anti-F1°2 Antibody

| DILUTION | F1°2 | PT | AP2/C7OH | AP2/C12OH | AP2/C12NH2 | AP2/C23NH2 | AP2/C23-10 | AP2/C12N13 |
|---|---|---|---|---|---|---|---|---|
| 50 | 1.17 | 1.46 | 0.55 | 0.03 | 0.07 | 0.03 | 0.04 | 0.16 |
| 100 | 0.94 | 1.34 | 0.34 | 0.02 | 0.02 | 0.02 | 0.02 | 0.09 |
| 200 | 0.63 | 1.10 | 0.21 | 0.02 | 0.03 | 0.02 | 0.02 | 0.07 |
| 400 | 0.40 | 0.80 | 0.10 | 0.01 | 0.01 | 0.01 | 0.01 | 0.03 |
| 800 | 0.21 | 0.49 | 0.05 | 0.01 | 0.03 | 0.02 | 0.02 | 0.03 |
| 1600 | 0.10 | 0.23 | 0.02 | 0.01 | 0.01 | 0.00 | 0.01 | 0.02 |
| 3200 | 0.06 | 0.12 | 0.02 | 0.02 | 0.01 | 0.00 | 0.02 | 0.01 |
| BLANK | 0.01 | 0.01 | 0.00 | 0.00 | 0.00 | 0.00 | 0.01 | 0.02 |

TABLE II-continued

F1°2, PT, and Peptide Incubations with TA1-5e Ascites

| DILUTION X1000 | F1°2 | PT | AP2/C70H | AP2/C120H | AP2/C12NH2 | AP2/C23NH2 | AP2/C23-10 | AP2/C12N13 |
|---|---|---|---|---|---|---|---|---|
| 10 | 1.50 | 0.01 | 1.61 | 0.01 | 0.01 | 0 | 0 | 0 |
| 20 | 1.31 | 0.00 | 1.48 | 0.00 | 0.00 | 0 | 0 | 0 |
| 40 | 0.85 | 0.01 | 1.07 | 0.00 | 0.02 | 0 | 0 | 0 |
| 80 | 0.47 | 0.00 | 0.63 | 0.00 | 0.00 | 0 | 0 | 0 |
| 160 | 0.25 | 0.01 | 0.37 | 0.00 | 0.01 | 0 | 0 | 0 |
| 320 | 0.11 | 0.00 | 0.19 | 0.00 | 0.01 | 0 | 0 | 0 |
| 640 | 0.07 | 0.00 | 0.10 | 0.00 | 0.00 | 0 | 0 | 0 |
| BLANK | 0.00 | 0.00 | 0.00 | 0.00 | 0.00 | 0 | 0 | 0 |

10 minute incubation with substrate

It should be understood that this process is not limited to prothrombin activation fragments. We have used other synthetic peptides of activation fragments of other blood coagulation proteins, such as those from Protein C and Factor XIII to generate highly specific antibodies. In particular, this process should be well suited for quantitating the activation process of complement proteins and any zymogen which is activated to its enzymatic form via peptide-bond cleavage with the accompanying release of a free activation peptide.

EXAMPLE 1A

Monoclonal Antibody TA1-5e

A. Peptide Synthesis

A synthetic polypeptide, identical with the first seven amino acid residues on the carboxy terminus of F1.2, having the following amino acid sequence: CYS-GLY-ASP-ARG-ALA-ILE-GLU-GLY-ARG-OH, was prepared using the solid-phase synthesis procedures described by Hudson et al., *High Yielding Fully Automatic Synthesis of Cecropin A Amide and Analogues,* Peptide Chemistry, 413 (1985).

B. Extraction of Organic Impurities From the Synthetic Peptides 50 mg of the peptide formed in Example 1A, was dissolved in 1 ml of water and vortexed. Two drops of glacial acetic acid were added and the aqueous suspension was extracted with 1 ml of ethyl acetate. The mixture was centrifuged and the upper aqueous phase removed. The ethyl acetate lower phase was extracted with water and recentrifuged. The aqueous phases were removed, combined and freeze-dried.

C. Preparation of Synthetic Peptide-protein Conjugates

Synthetic peptide was attached to either ovalbumin or keyhole limpet hemocyanin (KLH) as described by Carlsson et al., *Protein Thiolation and Reversible Protein-Protein Conjugation. N-Succinimidyl 3-(2-pyridyldithio) propionate a New Heterobifunctional Reagent,* 173 Biochem. J. 723 (1978). The 2-pyridyl disulphide groups introduced into ovalbumin or KLH were reacted with the synthetic peptide. The released pyridine-2-thione was used to monitor the reaction and to determine the degree of peptide substitution on the carrier protein.

D. Mouse Immunization Schedule

Balb/c mice were administered the synthetic peptide/conjugate at a final concentration of 50 ug/ml. An emulsion was prepared with 0.2 ml immunogen, 3.2 ml 150 mM NaCl and 10×Complete Freunds Adjuvant. Each mouse received 0.5 ml of the emulsion IP. The immunization protocol spanned 89 days.

E. Coating of Microtiter Plates with Peptide Conjugates or F1.2

The synthetic peptide (C7COOH), described in section A above, conjugated to ovalbumin was diluted in a coating buffer. 1 ml of peptide-conjugate (0.76 mg/ml) was diluted 66-fold in coating buffer. 100 ul of this solution was added to each well of a 96-well plate. The plates were sealed and incubated for 16–18 hours at 4 C. The contents were aspirated and the plates were washed 1× with wash/storage buffer; sealed plates were then stored at 4 C.

Plates coated with F1.2 were prepared similarly as plates coated with the peptide-ovalbumin conjugate. F1.2 was diluted in coating buffer to a concentration of 1 ug/ml.

F. Mouse Serum Titration

The mice immunized with the specific peptide-KLH conjugate were tested to determine whether antibody to F1.2 was present. Mouse serum titers were determined by ELISA using F1.2 immobilized on microtiter plates. Tests to determine antibody specificity were carried out by incubation of serial 2-fold dilution of antisera in the presence of a constant amount of immobilized antigen. Dilutions of mouse antisera were usually tested between 1:100 to 1:1280, normal mouse serum was used as a negative control. Relative titers were evaluated according to the strength of the reaction.

G. Cell Fusion

Hybridomas that secret monoclonal antibodies to F1.2 were developed. Hybridomas were derived essentially as described by Kohler, G. and Milstein C., *Continuous Culture of Fused Cells Secreting Antibody of Predefined Specificity,* 256 Nature 495 (1975).

Spleen cells were obtained from a mouse which had completed the immunization schedule described in section D above. Prior to fusion, a blood sample was obtained by orbital sinus puncture and the serum was analyzed for the presence of antibody to F1.2 as described in section E above.

Spleen cells from these mice were fused with mouse myeloma cells using buffered polyethylene glycol. Hybrids were formed containing the combined genome of the parent cell lines. Cold, sterile salt solution buffered saline solution was added to the cell suspension to bring the volume to 45 ml. The suspension was centrifuged at 200×g, 0–5 C. for 10 minute. The supernatant was removed by aspiration and the cells were resuspended using cold, sterile buffered saline solution. The procedure was repeated and the cells were suspended in 30 ml cold, sterile buffered saline solution.

1. Myeloma Cell Preparation

HPRT-minus myeloma cells were suspended by gentle agitation with a pipet. The myeloma cells were centrifuged at 200×g, room temperature for 10 minutes at room temperature. The supernatant was removed using a sterile pipet.

2. The cell pellets were combined and resuspended in a 50 ml tube, using RPMI. The volume of the myeloma cell suspension was adjusted to approximately 50 ml. The suspension was again centrifuged at 200×g, room temperature for 10 minutes and the supernatant was removed. The cell pellet was resuspended in 30.0 ml of Roswell Park Memorial Institute media and an accurate cell count was obtained. The mixture was pipetted numerous times with a 20 ml pipet. At this point, the myeloma cells were held on ice until other fusion preparations were ready.

Fusion of the Spleen and Myeloma Cells

Typically, approximately $2 \times 10^8$ spleen cells were fused with $1 \times 10^7$ myeloma cells. Appropriate volumes of each cell suspension were combined in a 50 ml tube and centrifuges at 200×g, 0–5 C., 10 minutes. The supernatant was removed by aspiration. Fusion was begun with drop-wise addition to the pellet of 1–1.5 ml of the polyethylene glycol solution. The tube was gently swirled as the polyethylene glycol solution was added. The fusion reaction was stopped by the drop-wise addition of 10 ml of warm (37 C.) Roswell Park Memorial Institute media. Another 20 ml of Roswell Park Memorial Institute media was added to the post-fusion suspension. The suspension was centrifuged at 200×g, room temperature for 10 minutes.

Peritoneal macrophage cells, at a final concentration $2 \times 10^4$ macrophages/ml were suspended in 20 ml of HATG media (HAT media supplemented with 20% fetal bovine serum and glycine). The suspension was centrifuged and the supernatant was removed by aspiration; 10 ml of HAT media was used to gently resuspend the macrophage pellet. The macrophage suspension was added directly to the spleen/myeloma cell suspension; 1 ml of the spleen/myeloma/macrophage cell suspension was then pipetted into each well of a series of 24-well plates. The plates were incubated at 37 C. in a humid, 10% $CO_2$ incubator. Eight to twelve days after the fusion, the plates were visually scanned for hybridoma growth.

Hybridoma Selection

Selection for hybrids was accomplished using HAT medium. The HPRT-minus myeloma cell line does not survive HAT medium (which contains hypoxanthine, aminopterin and thymidine). These cells can not use endogenous hypoxanthine to produce purines, while aminopterin blocks endogenous synthesis of purines and pyrimidnes.

H. Antibody/screening

The plates prepared as in section E above were used to test for the presence of specific antibodies in various samples, (i.e. ascites, tissue culture media and/or mouse sera). Various dilutions of each sample were added (100 ul) to separate. wells of the coated plates; the plates were incubated at room temperature with constant shaking for 30–60 minutes. Subsequently samples were aspirated and the plates were washed 3× with rinse buffer.

Enzyme-Antibody Conjugate (EAC) Incubation

A goat anti-mouse immunoglobulin/peroxidase conjugate was used to detect the presence of mouse antibodies which had bound to the coated plates. 100 ul enzyme antibody conjugate diluted in enzyme-conjugate buffer was added per well. The contents were incubated 30–60 minutes with constant shaking at room temperature. Subsequently the contents were washed 3× with rinse buffer.

Substrate Incubation

The substrate was diluted in the appropriate buffer and 150 ul added per well. The contents were incubated for 30–60 minutes. The reaction was stopped with standard quench buffer and shaken for 10 minutes. Data from this ELISA was used to show the presence of monoclonal antibodies to F1.2. A typical antibody screening experiment is shown in Table III.

TABLE III

|   | 1 | 2 | 3 | 4 | 5 | 6 | 7 | 8 | 9 | 10 | 11 | 12 |
|---|---|---|---|---|---|---|---|---|---|----|----|----|
| TABLE OF ADSORBANCE VALUES ||||||||||||| 
| A | 0.061 | 0.056 | 0.408 | 0.064 | 0.010 | 0.012 | 0.012 | 0.037 | 0.017 | 0.016 | 1.178 | 0.013 |
| B | 0.038 | 0.042 | 0.036 | 0.037 | 0.010 | 0.050 | 0.928 | 0.006 | 0.016 | 0.004 | 1.009 | 0.009 |
| C | 0.099 | 1.263 | 0.045 | 0.019 | 0.023 | 0.022 | 0.037 | 0.015 | 0.010 | 1.061 | 0.004 | 0.001 |
| D | 0.034 | 0.510 | 0.011 | 0.018 | 0.013 | 0.007 | 0.007 | 0.003 | 0.011 | 0.021 | 0.080 | 0.003 |
| E | 0.066 | 0.072 | 0.061 | 0.003 | 0.015 | 0.012 | 0.036 | 0.041 | 0.003 | 1.106 | 1.008 | 0.009 |
| F | 0.098 | 0.074 | 0.093 | 1.185 | 0.021 | 0.007 | 0.002 | 0.010 | 0.017 | 0.006 | 1.105 | 0.012 |
| G | 0.081 | 0.030 | 0.012 | 0.526 | 0.016 | 0.015 | 0.010 | 0.011 | 0.004 | 1.066 | 0.003 | 0.002 |
| H | 0.062 | 0.347 | 0.326 | 0.041 | 0.423 | 0.124 | 0.837 | 0.063 | 0.011 | 0.001 | 0.087 | 0.004 |
| TABLE OF RANGES ||||||||||||| 
| A | 0 | 0 | 2 | 0 | * | * | * | 0 | * | * | 7 | * |
| B | 0 | 0 | 0 | 0 | * | 0 | 6 | * | * | * | 6 | * |
| C | 0 | 8 | 0 | * | * | * | 0 | * | * | 7 | * | * |
| D | 0 | 3 | * | * | * | * | * | * | * | * | 0 | * |
| E | 0 | 0 | 0 | * | * | * | 0 | 0 | * | 7 | 6 | * |
| F | 0 | 0 | 0 | 7 | * | * | * | * | * | * | 7 | * |
| G | 0 | 0 | * | 3 | * | * | * | * | * | 7 | * | * |
| H | 0 | 2 | 2 | 0 | 2 | 0 | 5 | 0 | * | * | 0 | * |

I. Production of Mouse Antibody in Mouse Ascites

Tissue Culture

Hybridoma cell suspensions were pooled and centrifuged in conical tubes for use in ascites induction. The tubes were centrifuged at 200×g, 2–8c, 7–10 minutes, returned to an icebath and the supernatant was removed by aspiration.

Four cell pellets were resuspended in a total of 10 ml of cold Dulbecco's Phosphate Buffered Saline. The volume was brought to 40 ml with additional cold Dulbecco's Phosphate Buffered Saline and the tube was recentrifuged. The supernatant was removed by aspiration and the cell pellet was washed two more times in the same manner; a sample of the second wash was saved to obtain a cell count using a hemocytometer.

Determination of Hybridoma Cell Count and Viability

For hemocytometer counting of the hyridoma cells, 50 ul of 0.02% Trypan Blue was mixed with 50 ul of the cell suspension from above. Cells were counted after having settled in the counting area for approximately 2 minutes. The counting methods follow those of Absher, M. Hemacytometer Counting-in: Kruse, P F and Patterson M K eds, *Tissue Culture Methods and Application*, Academic Press pp. 395–397 (1973).

Pristane Priming

The mice were injected intraperitoneally (IP) with a volume of pristane.

Primary Induction of Ascites

At least six weeks after priming with pristane, the mice were injected IP with a volume of hybridoma cells.

Ascites Harvest

Ascites fluid was collected from the mice when their abdomens became distended and firm to the touch. The ascites was collected by syringe and transferred to sterile screw-cap conical centrifuge tubes. After 24 hours at 2–8 C., the cellular debris in the ascites fluid was sedimented by centrifugation.

The supernatant ascites was transferred into a clean container using a Pasteur pipet. The volume was estimated and 25% sodium azide was added (4 ul 25% sodium azide per ml of ascites fluid) with swirling.

J. Affinity Data

The affinity constant for the TA1-5e monoclonal antibody was determined to be $5.37 \times 10^5$ L/M. This constant was obtained using the method described in Friguet, et al., *Measurements of True Affinity Constant in Solution of Antigen-Antibody Complexes by Enzyme-Linked Immunoadsorbent Assay,* 77, J. Immunol. Methods, 305 (1985).

K. Determination of Monoclonal Antibody Specificity

Microtiter plates were coated with either F1.2, C12N13/ovalbumin (a peptide corresponding to the carboxy terminus of F2 and the new amino terminus of thrombin), or C70OH/ovalbumin. Samples of various ascites were tested for their ability to bind to these various antigens. Briefly, ascites dilutions were added (100 ul), incubated 1 hour (room temperature), then the plates were washed 3x. Goat anti-mouse immunoglobulin/peroxidase conjugate was then added (100 ul). Following a 1 hour incubation, the plates were washed 3x. Peroxidase substrate was added and the plates were incubated for an additional 30–60 minutes to identify antibodies that bound. See Table IV showing specificity testing of TA1-5e and TA1-10 (a monoclonal antibody made according to the process disclosed in Example 1A).

TABLE IV

|  |  | TA1-5e | TA1-10 |
| --- | --- | --- | --- |
| TABLE OF LIMIT SYMBOLS | | | |
| NHP | A | — | — |
| F1.2 | B | +4 | +4 |
| C7OH | C | +4 | +4 |
| C12NH$_2$ | D | — | — |
| C23NH$_2$ | E | — | — |
| C12N13 | F | — | — |
| F2 | G | +4 | +4 |
| PT | H | — | — |
| TABLE OF ADSORBANCE VALUES* | | | |
| A | | 0.016 | 0.012 |
| B | | 0.658 | 0.624 |
| C | | 0.590 | 0.496 |
| D | | 0.019 | 0.020 |
| E | | 0.001 | 0.001 |
| F | | 0.004 | 0.001 |
| G | | 1.868 | 1.847 |
| H | | 0.007 | 0.004 |

*The numerical data corresponds to the ranges posted above.

L. Western Blot Test

Electrophoretic transfer was performed essentially according to the method of Towbin, *Electrophoretic Transfer of Proteins from Polyacrylamide Gels to Nitrocelullose Sheets: Procedure and Some Applications,* 76 PNAS (USA) 4350 (1979). Briefly, proteins are transferred from SDS polyacrylamide gels to nitrocellulose membranes. Remaining protein binding sites on the membrane are then blocked with a gelatin solution. The membranes are incubated 1 hour at room temperature with the appropriate antibody diluted in Tris gelatin buffer. The membranes are then washed and incubated for 1 hour with the appropriate secondary antibody-peroxidase conjugate diluted in Tris/gelatin buffer. Following a buffer rinse, binding of antibody was identified with the peroxidase substrate, 4-chloro-1-naphthol. SDS-PAGE was performed essentially by the method of Laemmli, U. K. Nature 227 (1971) 6328. See FIG. 3 for a comparison of CC1-5d with TA1-5e, showing that TA1-5e binds to proteins in the molecular weight range of the F1.2 fragment, while CC1-5d binds to proteins in the molecular weight range of prothrombin and F1.2.

EXAMPLE 1B

Monoclonal Antibody CC1-5D

Monoclonal CC1-5d was derived from mice immunized with fragment F1.2. Mouse serum titration, cell fusion, hybridoma selection, ascites production and characterization were performed essentially as described in sections E through M above.

A. Affinity Data

The affinity constant for this monoclonal antibody was determined to be $7.04 \times 10^8$ L/M. This constant was obtained using the method described in Friguet et al., *Measurements of the True Affinity of Antigen-Antibody Complexes by Enzyme-Linked Immunoadsorbent Assay,* 77, J. Immunol. Methods 305 (1985).

EXAMPLE 2

Rabbit Polyclonal Antibodies

A. Rabbit Polyclonal Antibody Preparation

Peptides were synthesized according to the procedure disclosed in Example 1A, Section A. Ovalbumin conjugates with peptide C7OOH were made according to Example 1A, Section C.

B. Rabbit Immunization Schedule

Rabbits were immunized by a series of subcutaneous injections in either Complete or Incomplete Freund's Adjuvant. Immunization spanned 38 days; at the end of this period, antiserum titers were checked.

Antisera from rabbits AB51-AB55 were tested serially at dilutions between 1:1000 to 1:64,000. Antibody dilutions were incubated for one hour at room temperature on microtiter plates coated with a variety of synthetic peptides or F1.2. The wells were washed three times with PBS containing 0.05% Tween 20 and incubated with goat anti-rabbit immunoglobulin/peroxidase for 1 hour. The wells were again washed three times as before and peroxidase was added for 15–30 minutes.

Rabbit antisera was generally found to have an adequate titer against F1.2 but unacceptable cross-reactivity to prothrombin. Rabbit polyclonal antibodies therefore require subsequent immunoadsorption in order to remove unwanted cross-reactivities.

EXAMPLE 3

Sandwich Assay Using Monoclonal Antibodies

Monoclonal TA1-5e is immobilized on a solid carrier, such as in microtiter wells. A sample of patient plasma containing F1.2 and other plasma proteins is then contacted with immobilized TA1-5e for a specified time and temperature (i.e. 2 hours at room temperature). At this stage insoluble complex is formed between immobilized TA1-5e and F1.2; any unreacted F1.2 is removed by washing the microwell.

A measured amount of monoclonal CC1-5d Fab fragment, covalently labelled with an enzyme such as alkaline phosphatase, is then added to the above insoluble complex and incubated for a specified time and temperature (i.e. 1 hour at room temperature). The unreacted portion of labelled CC1-5d is again removed by washing. The amount of bound, labelled antibody is determined using an alkaline phosphatase substrate, such as 4-methyl-umbelliferyll-phosphate.

The amount of bound, labelled antibody is directly proportional to the concentration of F1.2 in the test sample. FIG. 4 shows a typical dose response curve for F1.2 using the system described above.

EXAMPLE 4

Sandwich Assay Using Polyclonal Antibodies

Polyclonal antibodies derived from rabbits immunized with synthetic peptides are immunoadsorbed using a solid-phase prothrombin reagent. This procedure removes antibodies which are cross-reactive with prothrombin and retains those antibodies specific for F1.2.

A sandwich assay using polyclonal antibodies can be produced by immobilizing the above affinity-purified antibodies to a solid carrier. These antibodies serve as capture antibodies similarly as monoclonal TA1-5e. Sample is then contacted with the capture antibody to form an insoluble complex and the unreacted F1.2 is removed by washing. A measured amount of labelled affinity-purified polyclonal antibody to F1.2 is then added to the above complex. The unreacted portion of the labelled antibody is removed by washing and the amount of the bound, labelled antibody is determined using the appropriate detection system.

What is claimed is:

1. A sandwich assay for the determination of the presence or concentration of F1.2 polypeptide fragment in bodily fluids which contain prothrombin comprising:
   (a) eliciting monoclonal or polyclonal antibodies (antibody formation) to CYS-GLY-ASP-ARG-ALA-ILE-GLU-GLY-ARG-OH wherein said polyclonal antibodies are immunoadsorbed with prothrombin and fragments thereof so as to remove cross-reactive antibodies;
   (b) immobilizing said monoclonal or polyclonal antibodies on a solid carrier;
   (c) contacting said immobilized antibodies with said bodily fluid;
   (d) adding a tagged antibody specific for said F1.2 polypeptide fragment; and
   (e) determining the presence or concentration of said F1.2 polypeptide fragment from the presence or concentration of the tag detected.

2. A sandwich assay for the determination of the presence or concentration of F1.2 polypeptide fragment in bodily fluids which contain prothrombin comprising:
   (a) eliciting monoclonal or polyclonal antibodies (antibody formation) to ASP-ARG-ALA-ILE-GLU-GLY-ARG-OH wherein said polyclonal antibodies are immunoadsorbed with prothrombin and fragments thereof so as to remove cross-reactive antibodies;
   (b) immobilizing said monoclonal or polyclonal antibodies on a solid carrier;
   (c) contacting said immobilized antibodies with said bodily fluid;
   (d) adding a tagged antibody specific for said F1.2 polypeptide fragment; and
   (e) determining the presence or concentration of said F1.2 polypeptide fragment from the presence or concentration of the tag detected.

3. A monoclonal antibody produced by (made by the process comprising: producing) a hybridoma formed by the fusion of cells from a mouse myeloma and spleen cells from a mouse (animal) previously immunized with a synthetic polypeptide which has the amino acid sequence: CYS-GLY-ASP-ARG-ALA-ILE-GLU-GLY-ARG-OH wherein said antibody binds specifically to the sequence CYS-GLY-ASP-ARG-ALA-ILE-GLU-GLY-ARG-OH.

4. A monoclonal antibody produced by (made by the process comprising: producing) a hybridoma formed by the fusion of cells from a mouse myeloma and spleen cells from a mouse (animal) previously immunized with a synthetic polypeptide which has the amino acid sequence: ASP-ARG-ALA-ILE-GLU-GLY-ARG-OH wherein said antibody binds specifically to the sequence ASP-ARG-ALA-ILE-GLU-GLY-ARG-OH.

* * * * *